United States Patent [19]

Tokano et al.

[11] Patent Number: 4,499,056
[45] Date of Patent: Feb. 12, 1985

[54] CONTINUOUS STERILIZING APPARATUS USING HOT WATER

[75] Inventors: Motoharu Tokano; Keiichi Kushima, both of Tokyo, Japan

[73] Assignee: Q. P. Corporation, Tokyo, Japan

[21] Appl. No.: 545,942

[22] Filed: Oct. 26, 1983

[30] Foreign Application Priority Data

Mar. 18, 1983 [JP] Japan .................................. 58-44424

[51] Int. Cl.³ .............................................. A61L 1/00
[52] U.S. Cl. ...................................... 422/299; 422/304
[58] Field of Search ................. 422/299, 300, 302, 304

[56] References Cited

U.S. PATENT DOCUMENTS

| | | | |
|---|---|---|---|
| 2,154,978 | 4/1939 | Galvin | 422/304 |
| 2,660,512 | 11/1953 | Webster | 422/304 |
| 3,323,856 | 6/1967 | Guckel | 422/304 |
| 3,972,679 | 8/1976 | Ruig | 422/304 |

FOREIGN PATENT DOCUMENTS 1278910 1/1961 France ............................ 422/304

Primary Examiner—John Adee
Attorney, Agent, or Firm—Neuman, Williams, Anderson & Olson

[57] ABSTRACT

The present invention is a sterilizing apparatus for continuously sterilizing foods, medicines, chemicals, etc. in the manufacture of those products. A hot water storage vessel and a cooling water storage vessel are mounted within a pressure tank, and such products passes through the hot water storage vessel while being carried by chain and are thereby sterilized. The hot water storage vessel is covered with an outer frame assembly and a heat insulating material is inserted therebetween to minimize heat loss. Further, the bearings for supporting the rotating shaft of sprockets which guide the movement of the chain are attached not to the hot water storage vessel but to the outer frame assembly to prevent the bearings from being changed in position or distorted by heat, thereby assuring a smooth rotation of the sprockets.

6 Claims, 7 Drawing Figures

CONTINUOUS STERILIZING APPARATUS USING HOT WATER

This invention relates to a continuous sterilizing apparatus for sterilizing foods, medicines, chemicals, etc. continuously by using hot water under pressure.

BACKGROUND OF THE INVENTION

A continuous sterilizing apparatus in which a hot water storage vessel is mounted within a pressure tank held at a high pressure and an article to be sterilized is moved through the hot water in the hot water storage vessel by a conveyor means such as chain or the like and is thereby sterilized continuously, is already known.

In such conventional continuous sterilizing apparatus, the hot water storage vessel is formed of a thin plate material into a box-like shape and this box-like vessel is directly mounted within the tank. And in the case of mounting a cooling water storage vessel together with the hot water storage vessel, both are mounted in contact with each other within the tank. In a certain conventional construction, moreover, a cooling water is charged directly into the tank and the hot water storage tank is mounted within the tank while being surrounded with the cooling water. Consequently, the hot water in the hot water storage vessel is always in a state of heat dissipation and also in a state of being cooled by the cooling water. In any case, a very large heat loss has heretofore been unavoidable.

Further, according to the foregoing conventional continuous sterilizing apparatus, the article to be sterilized passes through both hot water and cooling water as mentioned above, and this movement of the article under sterilization is performed by means of chain, and since bearings are mounted directly in the hot water storage vessel, sprockets which guide the movement of the chain undergo a direct influence of heat. Besides, the chain has heretofore been driven by a single, rotatably mounted, driving sprocket. When the chain, which is fairly long, is driven by a single driving sprocket, a large force is exerted thereon, so it is necessary to use a strong and thick chain. But since the chain passes through both cooling water and hot water together with the article to be sterilized, the use of a thick chain, namely, the use of a chain having a large heat capacity, leads to a larger heat loss in the hot water and cooling water storage vessels.

Thus, the conventional continuous sterilizing apparatus inevitably undergoes a large heat loss which is attributable to the structure of the hot water storage vessel and also to the size of the chain. And in order to compensate for such heat loss, there has heretofore been consumed heat energy in an amount larger than necessary.

In an effort to remedy such drawback, the present inventor has previously proposed an invention (see Japanese Patent Laid Open Publication No. 129677/1982) in which a cooling water storage vessel and a hot water storage vessel are mounted separately from each other. the former having a double structure with a heat insulating material being packed therebetween to diminish heat loss, and plural sprockets are let serve as driving sprockets thereby permitting the use of a thinner chain to diminish heat loss induced by the chain. However, reduction in size and weight of chain and sprockets results in the chain and sprockets being easily affected by heat, so that there arises another problem such as elongation of the chain and distortion of the sprockets. This phenomenon tends to be conspicuous particularly in hot water sterilization under pressure, that is, when the chain and sprockets are driven in hot water at 100° C. or higher. In view of such an inconvenience, the present invention further improves the above invention to minimize the influence of heat upon sprockets and chain in hot water at 100° C. or higher.

SUMMARY OF THE INVENTION

It is therefore the object of the present invention to provide a continuous sterilizing apparatus in which the heat loss of a hot water storage vessel is reduced and that of a conveyor means such as chain which travels while carrying thereon an article to be sterilized is also kept to a minimum and in which the conveyor means can travel smoothly through both the inside and outside of the hot water storage vessel while being little influenced by heat in the hot water.

The present invention is a continuous sterilizing apparatus comprising a pressure tank; a hot water storage vessel for holding therein a hot water at a temperature capable of sterilizing an article to be sterilized, the hot water storage vessel being mounted within the pressure tank; a heat insulating material provided on the outer periphery of the hot water storage vessel; an outer frame assembly mounted independently of and along side walls of the hot water storage vessel in spaced relation from the latter so that the heat insulating material is accommodated within the spacing; a cooling water storage vessel mounted within the pressure tank separately from the hot water storage tank; a conveyor means for holding and conveying the article to be sterilized through the cooling water in the cooling water storage vessel and also through the hot water in the hot water storage tank; a group of many sprockets serving as a guide for movement of the conveyor means, said group of many sprockets being disposed at appropriate intervals at least within the hot water storage vessel and the cooling water storage vessel; rotating shafts serving as rotating centers of the sprockets of the sprocket group; and bearings for rotatably supporting the rotating shafts, the bearings being attached to the outer frame assembly.

Thus, in the present invention, a hot water storage vessel and a cooling water storage vessel are mounted separately from each other within a pressure tank. The hot water storage vessel is retained its heat as far as possible by being packed with a heat insulating material such as asbestos, glass wool or the like on its outer periphery, for example, on its side plates, bottom plate or cover plate. Along side walls of hot water storage vessel is mounted an outer frame assembly independently of the same vessel while leaving a spacing for the heat insulating material.

The article to be sterilized, which is placed if necessary in a container such as a retainer or the like, is carried by a conveyor means such as chain or the like which passes successively through hot water in a hot water storage vessel and cooling water in a cooling water storage vessel, both vessels being held in a pressurized stage. As a guide for this conveyor means there are used many sprockets, which are provided a total of two for each rotating shaft in positions near both ends of the same shaft. Both ends of each rotating shaft extend at least through sides of the hot water storage vessel and supported on bearings attached to the outer frame assembly.

In each portion of the hot water storage vessel through which there extends the rotating shaft is fitted a pipe (sleeve) to prevent water leakage, with the fore end of the pipe being fixed to the bearing which is attached to the outer frame assembly, thereby allowing the bearing to serve as a water-leakage-proof sealing bearing.

Moreover, it is desirable that the above bearing be a self-aligning bearing and that a chain tension adjuster for adjusting the tension of the chain between sprockets be attached at its base portion to the outer frame assembly and be connected with the rotating shaft.

It is further desired that the outer frame assembly comprise a framed steel such as a framed wide flange beam and that for the purpose of reinforcement another steel be attached to at least the portions of the framed steel where the bearings and chain tension adjuster are mounted.

DESCRIPTION OF THE PREFERRED EMBODIMENTS

Figure 1:
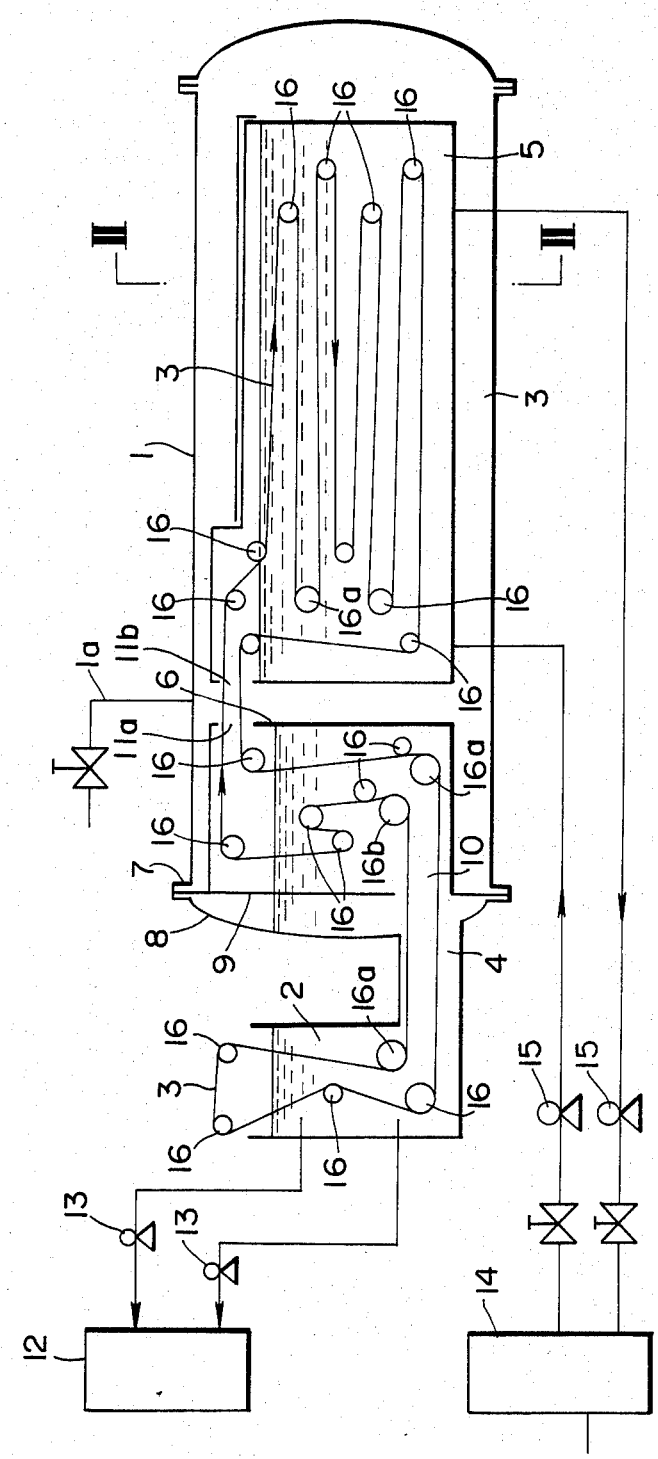
FIG. 1 is a sectional view of the entirety of a continuous sterilizing apparatus according to an embodiment of the present invention.

FIG. 1 is a sectional view of a continuous sterilizing apparatus according to the present invention, in which a pressure tank 1 with a high pressure pipe 1a from a high pressure pump (not shown) being connected thereto and a loading/unloading water vessel 2 are interconnected through an intermediate portion 4. A chain 3, which is mounted as shown, travels as indicated with arrows. In the position of the loading/unloading water vessel 2 an article to be sterilized (not shown) is loaded onto the chain 3 and unloaded therefrom after stetilization. In the intermediate portion 4 is incorporated a pressure cut-off mechanism (see Japanese Patent Laid Open Publication No. 117331/1982) to prevent the pressure in the pressure tank 1 from reaching the water vessel 2.

Figure 6:
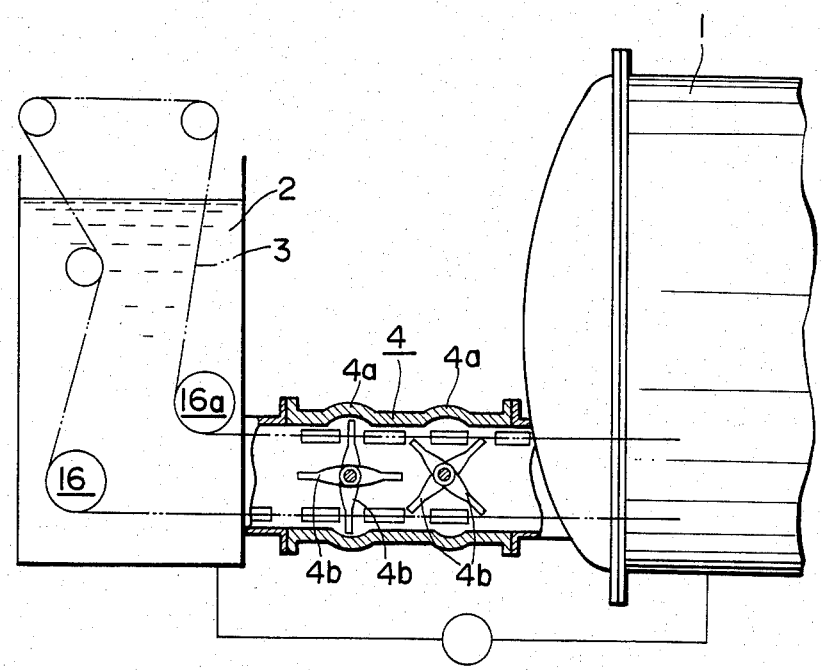
FIG. 6 is a sectional view of an intermediate portion showing a pressure cut-off mechanism.
Figure 7:
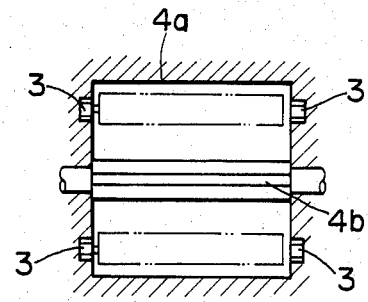
FIG. 7 is a longitudinally sectional view of the intermediate portion.

The pressure cut-off mechanism is of such a structure as shown in FIG. 6 and it will now be explained briefly. In upper and lower portions of the intermediate portion 4 are formed at least two casing portions 4a each in such a cylindrical shape as crosses this portion. In each casing portion 4a are mounted two or more blades 4b adapted to rotate about the center of the cylinder while the tip ends thereof are in contact with inner walls of the casing portion 4a. The blades mounted in each casing portion 4a rotate in the same direction, and any one of them is sure to be in contact at its tip ends with the upper and lower inner walls of the casing portion to cut off pressure. The chain passes through a groove formed in a side wall of the intermediate portion 4 while carrying thereon the article to be sterilized so that it does not cross the blades.

Within the pressure tank 1 are mounted a hot water storage vessel 5 and a cooling water storage vessel 6. The cooling water storage vessel 6 is a box-like vessel attached to a disc 9 which is fixed at its peripheral portion together with an end plate 8 to a flange 7 formed on the side of the intermediate portion 4 between the tank 1 and the loading/unloading water vessel 2. A window 10 is formed in the portion of the disc 9 opposed to the intermediate portion 4. Also in the right-hand upper end portion of the cooling water vessel 6 and the left-hand upper end portion of the hot water storage vessel 5 both in the figure there are formed windows 11a and 11b, respectively, for passing therethrough of the chain 3. The interior of the hot water storage vessel 5 and that of the cooling water storage vessel 6 are maintained in a pressurized state through those windows 11a and 11b. The cooling water storage vessel 6 is connected to the loading/unloading water vessel 2 through the window 10 formed in the disc 9 and further through the intermediate portion 4, whereby cooling water is fed thereto from the vessel 2 through a water passage. The cooling water in the loading/unloading water vessel 2 is recycled by means of a pump 13 so as to be cooled continually by a cooling tower 12. The pressure cut-off mechanism of the intermediate portion 4 forms a water passage which, as previously noted, intercepts pressure but allows passing therethrough of the article to be or after sterilized. Cooling water can be fed from the loading/unloading water vessel 2 to the cooling water vessel 6 through the water passage shown in FIG. 6, whereby both vessels can be maintained at about the same water level. On the other hand, hot water is fed from a hot water tank 14 to the hot water storage vessel 5 as necessary by two pumps 15. Moreover, through a steam pipe (not shown) the temperature of hot water can be further raised within the hot water storage vessel 5.

The chain 3 is moved in a predetermined direction by a group of many sprockets 16a, 16b, 16, ..., in which the numerals 16a and 16b represent driving sprockets. Four sprockets are mounted at each of both right and left end portions in the hot water storage vessel 5 so that the article being sterilized reciprocate over almost the entire right and left upper width in the figure. Among those eight sprockets, the second and fourth sprockets from the top of the left side are driving sprockets. Also in the cooling water storage vessel 6 and the loading/unloading water vessel 2 are mounted many sprockets for guiding the chain 3 as shown in the figure, among which a sprocket 16b mounted within the cooling water storage vessel is a main driving sprocket connected directly to a motor (not shown) provided outside the pressure tank. The driving sprockets 16a in the hot water storage vessel 5 are connected to the driving sprocket 16b through a belt or the like by utilizing the space formed between the hot water storage vessel and the outer frame assembly mounted along the outer periphery thereof. Further, a sprocket 16a mounted within the loading/unloading water vessel 2 is connected to the sprocket 16b through a belt at the exterior of the pressure tank.

Figure 2:
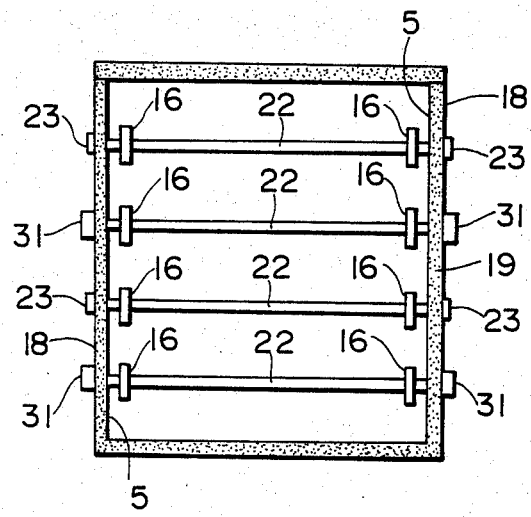
FIG. 2 is a sectional view taken on line II—II of a hot water storage vessel used in the apparatus.
Figure 3:
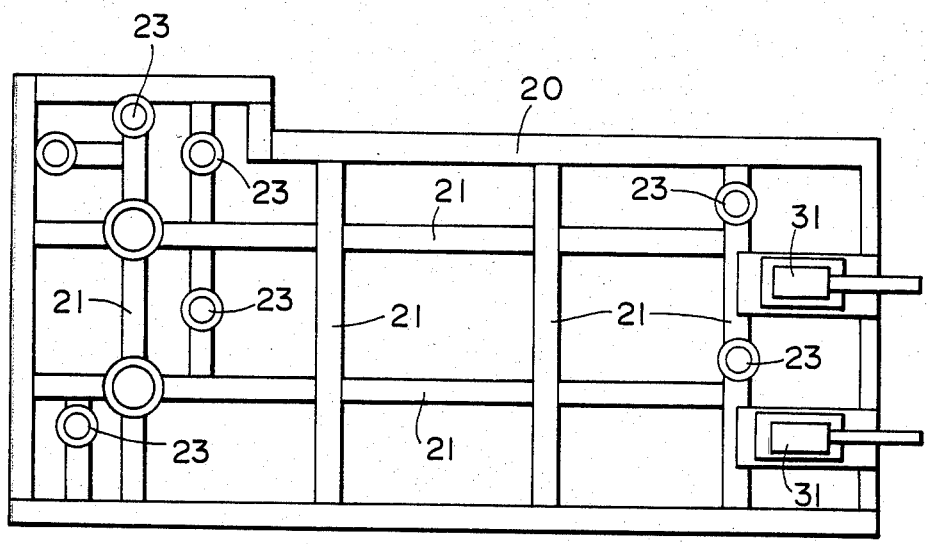
FIG. 3 is a side view of the hot water storage vessel.

As shown in FIG. 2, the hot water storage vessel 5 is formed of a metallic plate into a box-like shape, and outside and along the vessel 5 is mounted an outer frame assembly 18 in a surrounding relation to the same vessel, with a heat insulating material 19 such as asbestos or the like being packed between the vessel 5 and the outer frame assembly 18. The outer frame assembly 18 may be formed of a metallic plate into a box-like shape, but in this embodiment, as shown in FIG. 3, its surrounding portion is framed at 20 by steel such as a wide flange beam, angle or the like, and for the purpose of reinforcement, beams 21 formed of steel such as a wide flange beam or the like are disposed lengthwise and crosswise, to constitute a frame assembly, and a thin metallic plate is attached to the other portions than those steel frame and beams in order to hold down the heat insulating material 19. At least the portions where bearings of rotating shafts of sprockets and chain tension adjusters as will be described later are mounted, are reinforced with the above steel product. The thus-assembled outer frame assembly 18 is then subjected to a so-called annealing treatment at about 400° C. to remove strain.

Figure 4:
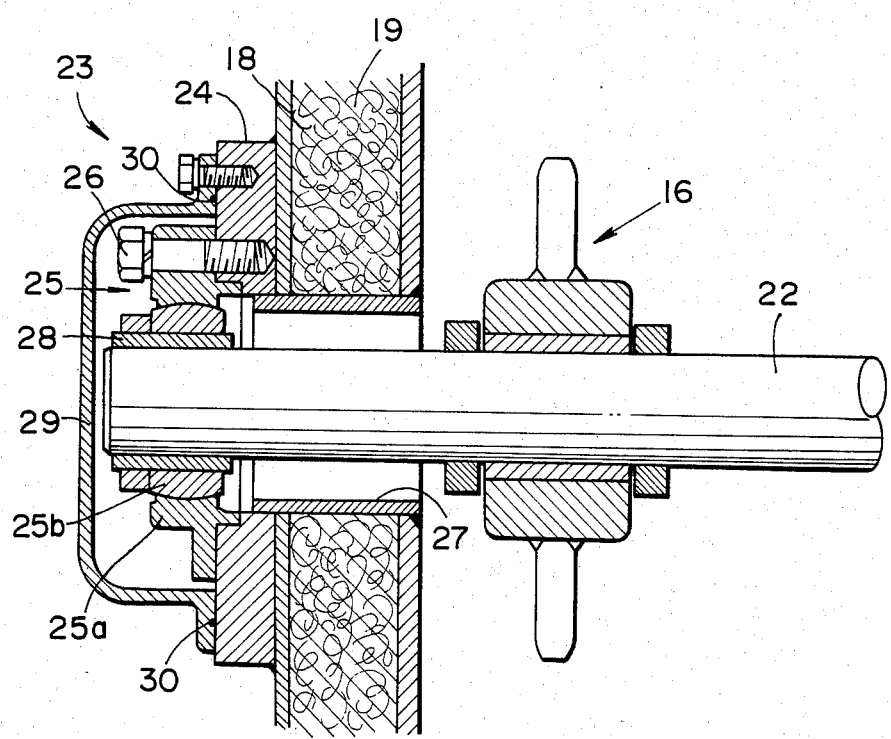
FIG. 4 is a sectional view of a bearing portion.
Figure 5:
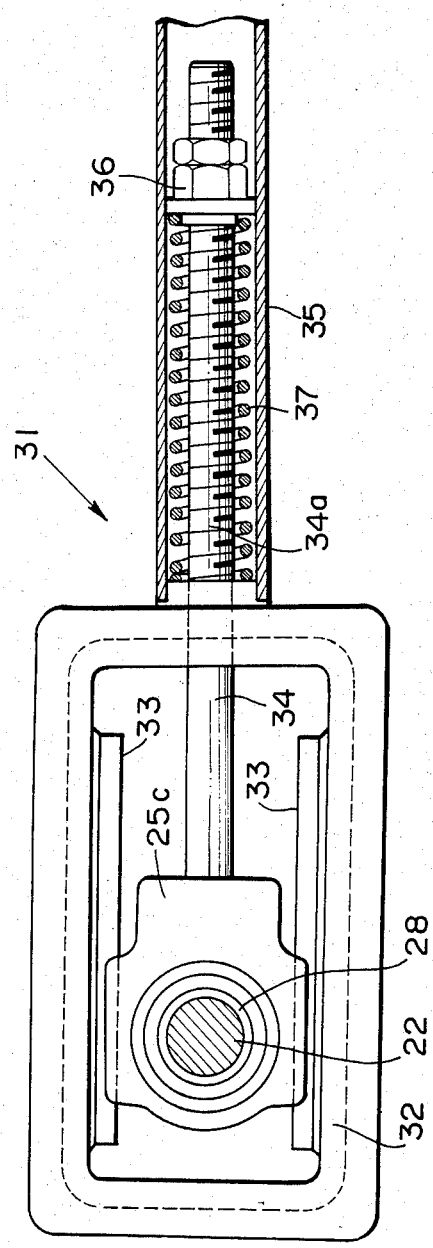
FIG. 5 is a partially sectional side view of a chain tension adjuster.

Each sprocket 16, as shown in FIG. 2, is mounted on a rotating shaft 22 so that it can rotate together with the shaft 22. The rotating shaft 22 is supported rotatably by bearing portions 23 which are attached to the outer frame assembly 18. The bearing portions of the rotating shafts of other sprockets than the driving sprockets 16a and 16b are constructed as shown in FIG. 4. That is, a seat plate 24 formed of a metal is fixed by welding to the outer frame assembly 18, and a self-aligning bearing 25 is secured thereto with bolt 26, and a pipe 27 for insertion therethrough of the rotating shaft 22 is attached to the seat plate 24 from the hot water storage vessel 5 through the outer frame assembly 18. The circumference of the pipe 27 on the vessel 5 side is fixed to the vessel by welding to prevent leakage of hot water. As is generally known, the self-aligning bearing 25 comprises a base portion 25a which is fixed to the seat plate 24 and a rotating portion 25b which is fixedly mounted on an end portion of the rotating shaft 22 through a collar 28. This structure prevents leakage of hot water to the exterior, but by way of precaution, these portions are covered with a cover 29 through an O-ring 30 so that even in the vent of hot water oozing out it may not leak at all to the exterior.

The bearing portions of the driving sprockets also have about the same construction as above, with difference being recognized only in the structure of cover. More specifically, a hole is formed centrally in the cover for insertion therethrough of the rotating shaft 22, and the length of the rotating shaft is made large enough to project to the exterior of the cover, with a driving sprocket being mounted on the projecting end of the rotating shaft.

The chain engages each sprocket as shown in FIG. 1. In this case, in order that the chain 3 may be maintained in an appropriate tension without becoming too loose or too tight, a chain tension adjuster is attached to both ends of some of the rotating shafts 22. In this embodiment, such chain tension adjuster 31 is mounted in two places as shown in FIG. 3.

In each of the portions of the hot water storage vessel 5 and outer frame assembly 18 where the chain tension adjuster 31 is mounted, there is formed a long hole (not shown) so that the rotating shaft 22 can move horizontally. The chain tension adjuster is also provided with a bearing for supporting the rotating shaft 22, which bearing itself is a self-aligning bearing like the foregoing bearing, but is constructed so that its base portion 25c can move along rails 33 laid on side walls of a case 32. Further, a slide shaft 34 is attached to the base portion 25c to thereby move the bearing and hence the rotating shaft 22. The greater part of the slide shaft 34 comprises a screw portion 34a, which is inserted into a cylinder 35 attached to the case 32. Further, a nut 36 is threadedly engaged with the screw portion 34a, and a spring 37 is inserted between the nut 36 and the surface of the case 32 along the slide shaft 34. The position of the bearing is controlled by the nut 36 and the spring 37.

The bearings 23 described in this embodiment are for the sprockets disposed in the hot water storage vessel 5. The bearings used in the cooling water storage vessel 5 are of the same structure. Since the cooling water storage vessel 6 is less distorted by heat, there may be used other conventional bearings, and the rotating shaft passing portions of the hot water storage vessel may be sealed with an elastic sealing material such as a rubber seal or the like.

The chain 3 is moved as indicated with arrows by means of the driving sprocket 16b which is connected to a motor (not shown) outside the pressure tank 1, and the driving sprockets 16a which are connected to the driving sprocket 16b by chain belts within the pressure tank. An article to be sterilized (not shown) is loaded onto the chain 3, then with movement of the chain 3, it is conducted through the cooling water storage vessel 6 into the hot water storage vessel 5. Hot water heated to about 130°~140° C. is contained in the hot water storage vessel 5, so that while passing through the vessel 5, the article to be sterilized is sterilized. The article thus sterilized is then cooled while passing through the cooling water storage vessel and then unloaded in the loading/unloading water vessel 2. Thus, the chain 3 travels while being pulled by the driving sprockets 16a and 16b. The sprockets or rotating shafts 22 are loaded in proportion to the weight of the chain itself and that of the article being sterilized. It goes without saying that all of these loads are imposed on the bearings 23. Besides, as shown in FIG. 2, the sprockets are mounted in the vicinity of both end portions of the rotating shaft 22, so even under a slight influence of elongation of the chain or distortion of the sprockets induced by heat, the loads imposed on the bearings are no longer uniform. Further, since the hot water storage vessel 5 contains hot water heated to as high as 140° C., it is possible that the hot water storage vessel itself will be thermally deformed to cause a positional shift of the right and left bearings.

According to this embodiment, however, since the hot water storage vessel 5 and the outer frame assembly 18 are constituted as completely separate independent components and with the heat insulating material 19 being packed therebetween a thermal deformation of the vessel 5 would be restricted to the same vessel, not reaching the outer frame assembly 18. Besides, since the bearings 23 are attached to the outer frame assembly 18, the rotating shafts 22 can be rotated smoothly without being influenced by such thermal deformation.

Moreover, a slight distortion of the rotating shaft 22 induced by load can be fully compensated because the self-aligning bearing 25 is used as the bearing 23, thus permitting a smooth rotation of the rotating shaft 22.

Further, since the hot water storage vessel 5 is covered with the heat insulating material 19 and a pressurized air layer is formed between the vessel 5 and the inner wall of the pressure tank, it is possible to minimize the transfer of heat to the exterior of the tank.

As a matter of course, moreover, in case the chain 3 is too loose or too tense and does not move smoothly, this can be corrected by operating the chain tension adjuster 31 to adjust the position of the bearing of the rotating shaft 22 to which it is attached, into the position in which the rotating shaft rotates most smoothly. This positional adjustment for the bearing by the chain tension adjuster 31 can be done by the nut 36, and no special explanation will be needed on this respect.

According to the present invention, as set forth hereinabove, the outer frame assembly is provided independently of the hot water storage vessel and the bearings of the rotating shaft of sprockets are attached to the outer frame assembly which is not directly affected by the temperature of hot water. Consequently, the rotating shaft is not influenced by a thermal distortion, it is possible to ensure a smooth rotation of the sprockets which guide the movement of the chain, and hence the rotation of the rotating shaft, and even if the chain is reduced in weight and size, it is possible to maintain the movement of the chain always in a stable state, thus permitting a remarkable saving in power cost.

Additionally, since the cooling water storage vessel and the hot water storage vessel are completely separated from each other within the pressure tank and the outer frame assembly is provided independently of the hot water storage vessel and with a heat insulating material being packed therebetween, the effect of heat insulation from the exterior of the pressure tank is so much enhanced and heat loss can be diminished. Thus, the continuous sterilizing apparatus according to the present invention can exhibit a high energy saving effect as a whole.

While only a limited number of embodiments of this invention have been disclosed, it is to be understood that this invention is not limited thereto but further includes that which falls fairly within the following claims.

We claim
1. A continuous sterilizing apparatus comprising:
a pressure tank;
a hot water storage vessel for holding therein hot water at a temperature capable of sterilizing an article to be sterilized, said hot water storage vessel being mounted within said pressure tank;
a heat insulating material provided on the outer periphery of said hot water storage vessel;
an outer frame assembly mounted independently of and along side walls of said hot water storage vessel in spaced relation from the latter so that said heat insulating material is accommodated within the spacing;
a cooling water storage vessel mounted within said pressure tank separately from said hot water storage tank;
a conveyor means for holding and conveying the article to be sterilized through the cooling water in said cooling water storage vessel and also through the hot water in said hot water storage tank;
a group of many sprockets serving as a guide for movement of said conveyor means, said group of many sprockets being disposed at appropriate intervals at least within said hot water storage vessel and said cooling water storage vessel;
rotating shafts serving as rotating centers of the sprockets of said sprocket group; and
bearings for rotatably supporting said rotating shafts, said bearings being attached to said outer frame assembly.

2. A continuous sterilizing apparatus according to claim 1, wherein said outer frame assembly comprises an outer framed steel such as an outer framed wide flange beam or the like and a reinforcing steel attached to said outer framed steel at least the portions where said bearings are mounted.

3. A continuous sterilizing apparatus according to claim 2, wherein said outer frame assembly has been subjected to an annealing treatment after framing.

4. A continuous sterilizing apparatus according to claim 1, wherein said bearings attached to said outer frame assembly each comprise a water-leakage-proof sealing bearing and wherein pipes for insertion therethrough of said rotating shafts are mounted between said hot water storage vessel and said bearings.

5. A continuous sterilizing apparatus according to claim 4, wherein said bearings each comprise a self-aligning bearing.

6. A continuous sterilizing apparatus according to claim 1, wherein said bearings on both ends of at least one said rotating shaft each comprise a chain tension adjuster capable of adjusting the mounting position of the bearing relative to said outer frame assembly.

* * * * *

UNITED STATES PATENT AND TRADEMARK OFFICE
CERTIFICATE OF CORRECTION

PATENT NO.   :   4,499,056
DATED        :   February 12, 1985
INVENTOR(S)  :   MOTOHARU TAKANO and KEIICHI KUSHIMA It is certified that error appears in the above-identified patent and that said Letters Patent is hereby corrected as shown below:

In the title or cover page, change "Tokano et al." to
    -- Takano et al. --.

Change the name of the first inventor "Motoharu Tokano"
    to -- Motoharu Takano --.

Column 1, line 61, after "other", the period (.) should
    be a comma (,).

Column 5, line 32, there should be a space between "25"
    and "which".

Signed and Sealed this

Twentieth   Day of   August 1985

[SEAL]

Attest:

DONALD J. QUIGG

Attesting Officer    Acting Commissioner of Patents and Trademarks